United States Patent [19]

Neimark et al.

[11] Patent Number: 4,748,002
[45] Date of Patent: May 31, 1988

[54] SEMI-AUTOMATIC, SOLID-PHASE PEPTIDE MULTI-SYNTHESIZER AND PROCESS FOR THE PRODUCTION OF SYNTHETIC PEPTIDES BY THE USE OF THE MULTI-SYNTHESIZER

[75] Inventors: Jean Neimark; Jean-Paul Briand, both of Strasbourg, France

[73] Assignee: Centre National de la Recherche Scientifique (CNRS), Paris, France

[21] Appl. No.: 866,956

[22] Filed: May 27, 1986

[30] Foreign Application Priority Data

Jun. 3, 1985 [FR] France ................... 85 08438

[51] Int. Cl.$^4$ ........................... C07K 1/04; C07K 1/06; C07K 1/10; B01J 8/02
[52] U.S. Cl. ..................... 422/116; 422/131; 530/333; 530/334; 525/54.11
[58] Field of Search ............... 530/333, 334; 525/54.1, 525/54.11; 422/116, 131

[56] References Cited

U.S. PATENT DOCUMENTS

| | | | |
|---|---|---|---|
| 3,557,077 | 1/1971 | Brunfeldt et al. | 530/334 |
| 3,715,190 | 2/1973 | Park et al. | 422/100 |
| 4,517,338 | 5/1985 | Urdea et al. | 525/54.1 |
| 4,552,922 | 11/1985 | Patchornik et al. | 525/54.1 |
| 4,598,049 | 7/1986 | Zelinka et al. | 525/54.1 |

FOREIGN PATENT DOCUMENTS

| | | |
|---|---|---|
| 0042792 | 12/1981 | European Pat. Off. . |
| 0130739 | 1/1985 | European Pat. Off. . |
| 2554820 | 5/1985 | France . |

OTHER PUBLICATIONS

"An Automatic Apparatus for the Synthesis of Peptides Using Resin Coated Glass Beads in the Form of a Packed Bed", *Journal of Chromatographic Science*, vol. 10, Jun. 1972, by R. P. W. Scott et al., pp. 384–391.

*Primary Examiner*—Delbert R. Phillips
*Assistant Examiner*—Nathan M. Nutter
*Attorney, Agent, or Firm*—Young & Thompson

[57] ABSTRACT

A semi-automatic, solid phase peptide multi-synthesizer is characterized in that it is principally constituted by chemical reactors (2), connected to volumetric solvent proportioners (1) disposed above the said chemical reactors (2) and below a solvent selector (4) supplied with solvent by solvent containers (6) under pressure of nitrogen distribution cylinders (3), as well as a center for adjustment and regulation of very low pressure nitrogen (5), are sequentially controlled by a programmable automation (7) or a microcomputer assuring the carrying out of the synthesis technique. The maximum number of volumetric solvent proportioner (1)—chemical reactor (2) assemblies is equal to the maximum number of peptides which may be produced simultaneously.

9 Claims, 6 Drawing Sheets

SEMI-AUTOMATIC, SOLID-PHASE PEPTIDE MULTI-SYNTHESIZER AND PROCESS FOR THE PRODUCTION OF SYNTHETIC PEPTIDES BY THE USE OF THE MULTI-SYNTHESIZER

The present invention, realized in laboratory LP 6201 of the Institute of Molecular and Cellular Biology of the NATIONAL CENTER FOR SCIENTIFIC RESEARCH (NCSR), concerns the chemical synthesis of peptides, and has as an object a peptide multi-synthesizer comprising means for assuring the simultaneous synthesis of a variable number of peptides in differing quantities and having identical or different sequences.

At present, none of the existing apparatus permits the simultaneous synthesis of more than two peptides with different sequences. The synthesizers which exist are either mono-synthesizers, or bi-synthesizers, and are manual, semi-automatic or automatic. The mono-synthesizers are capable of synthesizing only a single peptide at a time, and the bi-synthesizers, which use two reactors, can synthesize simultaneously only two different peptides. But, the synthesis of a peptide of 20 to 30 amino acids with verification of each amino acid linkage generally requires about ten days. With such apparatus, it is reasonable to expect a production of only four synthetic peptides per month. Moreover, it must be noted that each of the automatic apparatus on the market at present does not effect control tests at the essential stages of the synthesis.

The present invention has as an obect to permit simultaneously the synthesis of a variable number of peptides with identical or different sequences according to a common synthesis technique.

Specifically, it has as an object a semi-automatic, solid-phase peptide multi-synthesizer, characterized in that it is principally constituted by chemical reactors connected to volumetric solvent proportioners disposed above the said chemical reactors and below a solvent selector supplied with solvent by solvent containers under pressure of nitrogen, by distribution cylinders, as well as by a center for adjustment and regulation of very low pressure nitrogen, these means being sequentially controlled by a programmable automaton or a microcomputer assuring the carrying out of the synthesis technique, and the maximum number of volumetric solvent proportioner-chemical reactor assemblies as being equal to the maximum number of peptides which may be simultaneously synthesized.

In the past years, the chemical synthesis of peptides has advanced considerably. Specifically, it has been established that numerous peptides play a fundamental role in the communication between neurons. The use of synthetic peptides has thus permitted rapid progress in the understanding of the mechanism of action of neuropeptides and in their therapeutic utilization.

But the use of synthetic peptides has similarly taken a dominant place in several other fields. In immunology, this technology constitutes a future path toward the obtention of synthetic vaccines. There are synthesized, in this case, peptides corresponding to the antigenic regions of viral proteins. Recent results show that the coupled peptides, injected in an animal, may protect it from viral infection. Use of such synthetic vaccines will permit avoiding the inherent problems in the production of known vaccines, particularly the accidental persistence of pathogenic agents in the inactivated virus preparations, and the injection of viral nucleic acid that is always present in these preparations.

In molecular biology, thanks to the developments of genetic engineering, it is possible to arrange relatively easily the coding gene sequence for functional proteins or structure proteins. Thus, these nucleotidic sequences are decoded and the amino acid sequences of these proteins are obtained without having had either to isolate or to purify them. It is nevertheless necessary to know if these proteins are actually present in the cellular system under study. It is at this stage that the use of synthetic peptides intervenes. The peptidic fragments previously mentioned as being probable antigenic determinants of the protein under study are synthesized, and they are coupled to a carrier protein before being injected into the animal. Given that the anti-peptide antibodies are capable, in most cases, of identifying the native protein, it can therefore be known if the protein is present or not in the cell. With the aid of immunoadsorption columns, one may thus envision purifying the protein in question starting from a crude cellular extract. It is similarly possible to observe, for example, the fate of various regions of a protein when this latter undergoes a process of maturation.

Various synthesis techniques are known. The technique most used currently is that developed by Merrifield. His principle is as follows:

The amino acids are sequentially added to the growing chain, the C-terminal extremity of which is connected to an insoluble solid support. All of the reactions take place in the same vessel and the excess reagents are eliminated by simple filtration and washings. The sequence of operations is effected in the following manner:

2. REMOVAL OF THE PROTECTING GROUP FROM THE NαAMINO GROUP OF AMINO-ACID 1

3. CONDENSATION OF THE NEXT BOC—AMINO ACIDS

Cycle repeated (n − 1 times)

4. LIBERATION OF THE PEPTIDE-REMOVAL OF THE PROTECTING GROUPS FROM THE SECONDARY GROUPS

The solid support is a polystyrene resin polymerized with 1% divinylbenzene and comprising a great number of groups capable of reacting with the —COOH group of the amino acids. During the condensation step, the Nα amino group of the added amino acid must be protected: the protecting group most used is t-butyloxycarbonyl (BOC). The secondary functional group is similarly protected during the entire synthesis. They are unblocked only at the time of the liberation of the peptide from the resin, by hydrofluoric acid.

The t-butyloxycarbonyl group is eliminated by acidolysis in a trifluoroacetic acid-dichloromethane system containing an anti-oxidizing agent. The amino group obtained in the form of a salt is then neutralized in the presence of a base such as N,N diisopropylethylamine. These two principal steps are separated by several washing steps. Then the deprotection reaction is verified by a test with ninhydrin.

The condensation agent used is N,N'dicyclohexylcarbodiimide which activates the carboxyl group of the t-butyloxycarbonyl protector-amino acid grouping to be added, in O-acyl urea. This intermediate may also be rapidly isomerized in inactive N-acyl urea.

The reaction conditions are as follows:

*t-butyloxycarbonyl-amino-acid group: molar excess ×3
*N,N'dicyclohexylcarbodiimide of the dichloromethane for 1 to 2 hours.

Variations of the coupling reaction consist in adding the amino acid in a pre-activated form. The two most used forms are the activated esters or the symmetric anhydrides of amino acids.

Whatever may be the method of coupling employed, the condensation reaction is verified by the test with ninhydrin. If the coupling reaction is not complete, a double condensation is effected, that is to say that the neutralization step is repeated. Specifically, it is possible that a slight percentage of peptide-resin remains in the salt form. The t-butyloxycarbonyl-amino-acid group and the N,N'dicyclohexylcarbodiimide are the added in 1.5 molar excess for 30 min. to 1 hour.

If the ninhydric test still remains slightly positive, the remaining free N amino groups are blocked, by an acetylation reaction, which could give rise to additional reactions at the time of subsequent condensations.

| *acetic anhydric | molar excess × 10 |
|---|---|
| *N,N diisopropylethylamine | molar excess × 11 | in dichloromethane for 10 min.

There exists a variant of the Merrifield technique proposed by Sheppard. The general principle is the same, but the nature of the protecting groups, the deprotecting solvents and if desired the resin, is changed.

Merrifield has elaborated this technique so as to permit its automation. Indeed, the quality of the final product, that is to say that of the pepetide obtained with an automatic, semi-automatic or manual synthesis apparatus is the same whatever may be the conception of the said apparatus, but the use of a manual synthesis apparatus requires attention such that the permanent presence of the operator is essential. Nevertheless, the use of an entirely automatic apparatus does not permit immediate quality control at each fundamental step of the synthesis and this is why the present invention concerns a semi-automatic peptide multi-synthesizer seeking the obtention of a final product of very high purity.

BRIEF DESCRIPTION OF THE DRAWINGS

The invention will be best understood thanks to the following description, which relates to preferred embodiments, given by way of non-limiting examples and explained with reference to the accompanying schematic drawings, in which.

DETAILED DESCRIPTION OF THE INVENTION

According to the invention, the peptide multi-synthesizer is principally constituted by chemical reactors 2 connected to volumetric solvent proportioners 1 disposed above the said chemical reactors 2 and below a solvent selector 4 supplied by solvent containers 6 under pressure of nitrogen, by distribution cylinders 3, as well as by a center for adjustment and regulation of very low pressure nitrogen 5, these means being sequentially controlled by a programmable automaton 7 or a microcomputer assuring the carrying out of the synthesis technique, and the maximum number of volumetric solvent proportioner 1-chemical rector 2 assemblies being equal to the maximum number of peptides which may be produced simultaneously.

Figure 1:
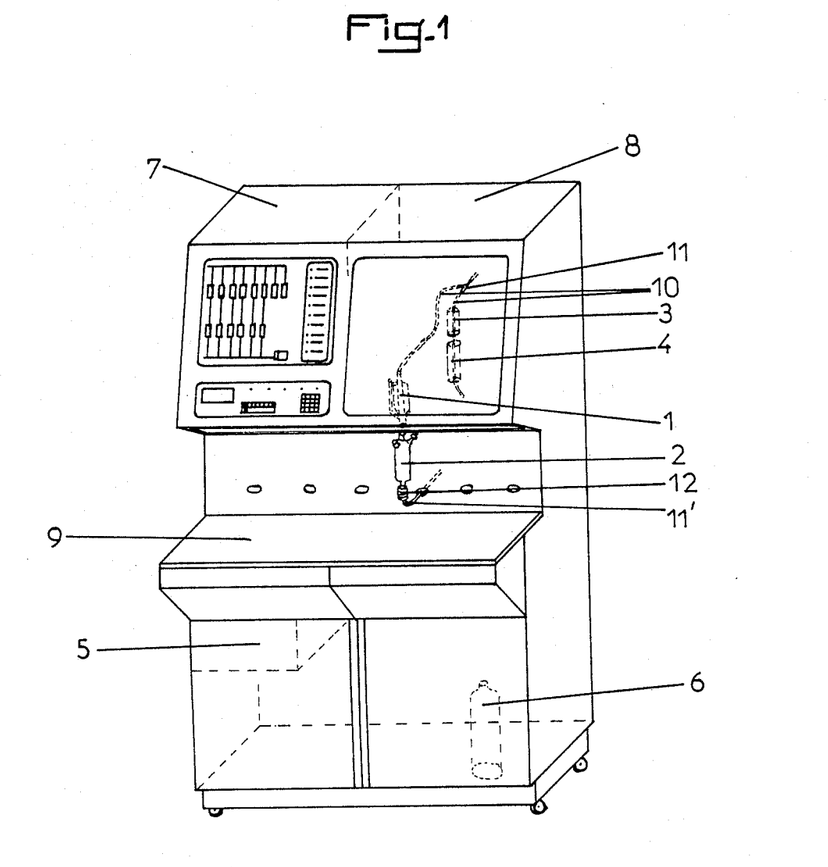
FIG. 1 is a perspective view of the peptide multi-synthesizer according the the invention.

As shown in FIG. 1, the peptide multi-synthesizer has a metallic frame 8 the lower part of which encloses the center 5 for adjustment and regulation of very low pressure nitrogen as well as the containers 6 of solvent under pressure of nitrogen, the central portion of which is constituted by a work table 9 behind which is found the region of the output valves of the chemical reactors 2 and above which is situated the region of the chemical reactors 2, and the upper part of which encloses the volumetric solvent proportioners 1, behind which is found the various distribution cylinders 3, the solvent selector 4, as well as the programmable automaton 7 or the microcomputer.

Figure 7:
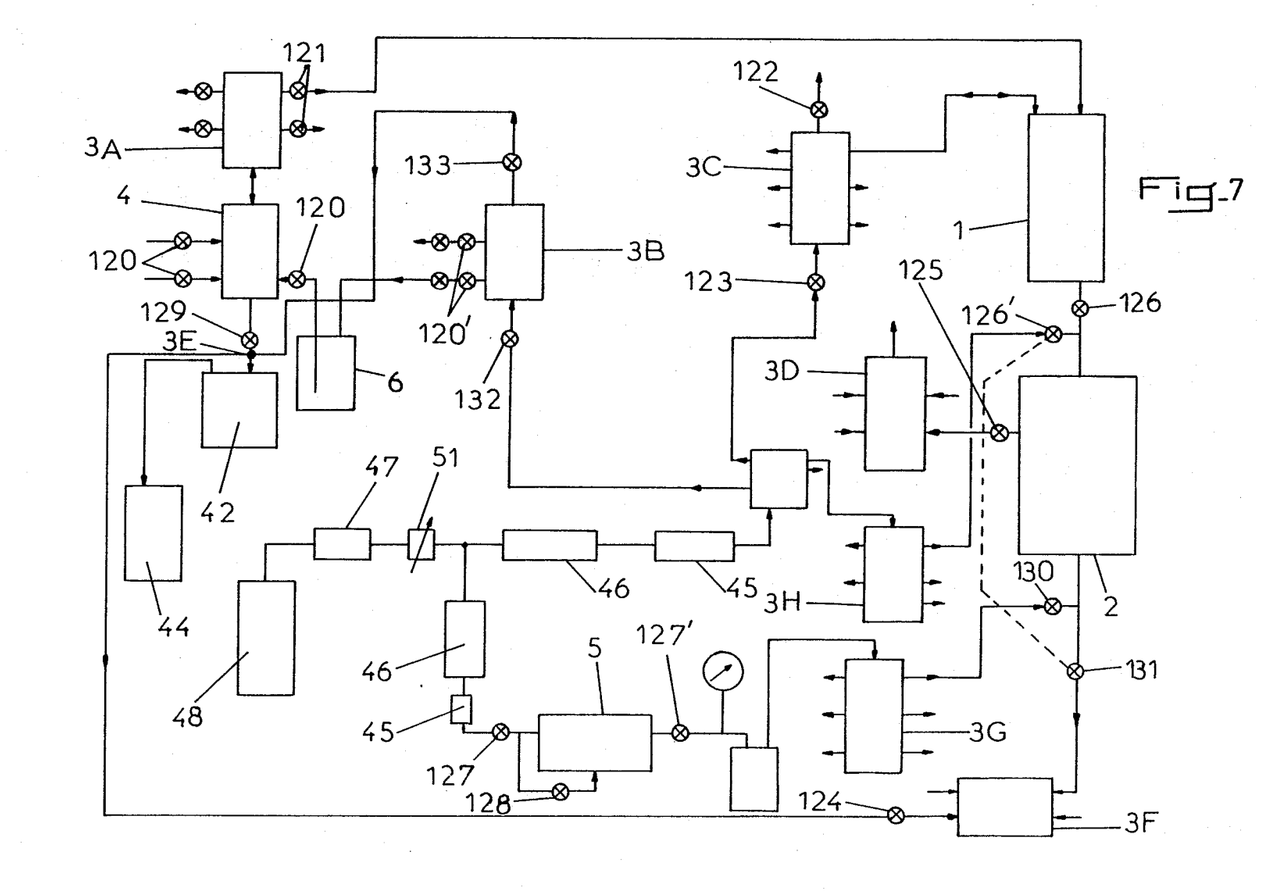
FIG. 7 is a view of the principal connection diagram for a volumetric solvent proportioner-chemical reactor.
Figure 8:
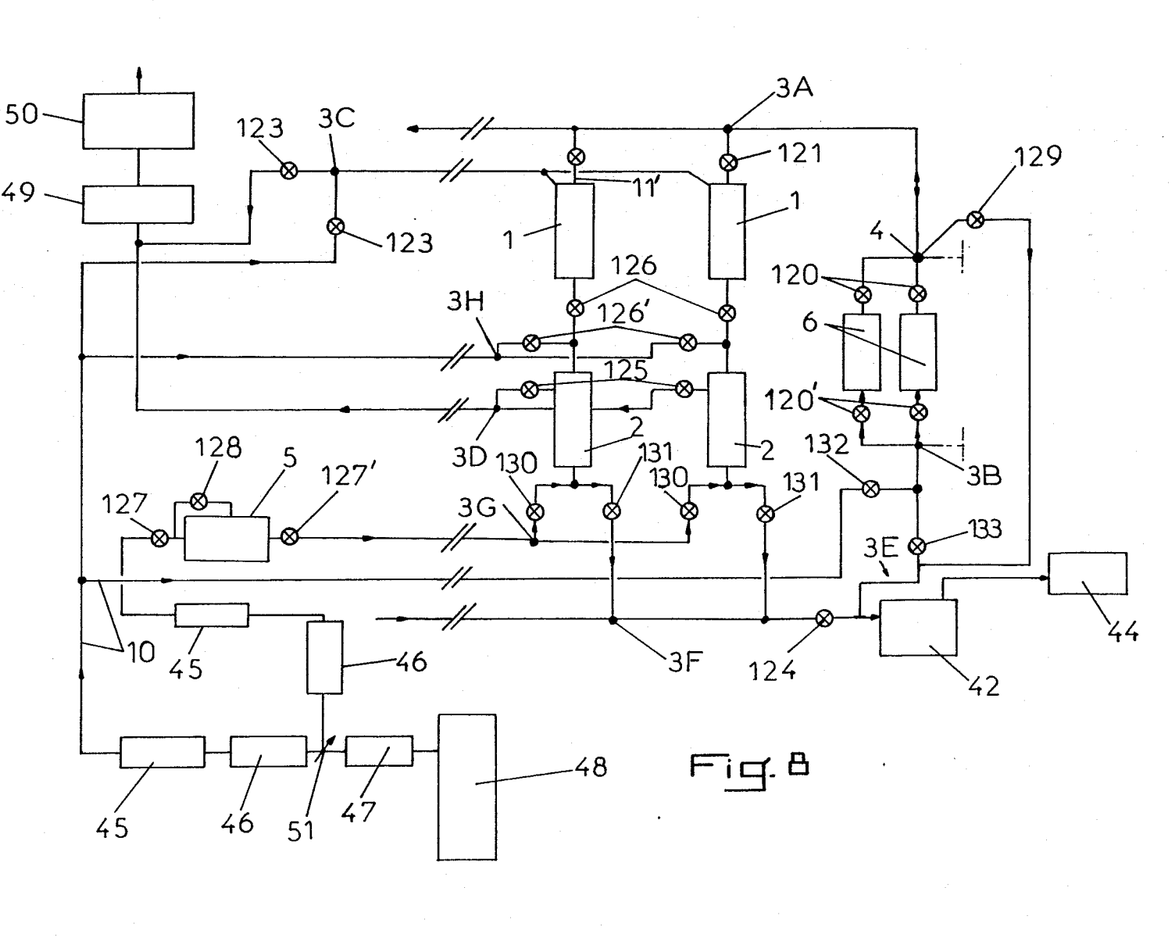
FIG. 8 is a view of the fluidic and pneumatic principle functioning diagram.

The front surface of the upper part has various dials, one dial in particular of which illustrating the synoptic diagram of the fluidic and pneumatic operation of the device, a dial for control and programming of the automaton as well as a dial for control of irregularities. The solvent containers 6 are disposed on the base of the metallic frame 8. All of the other elements, particularly the center 5 for adjustment and regulation, the volumetric solvent proportioners 1, the chemical reactors 2, the distribution cylinders 3, the solvent selector 4 and the programmable automaton 7 or the microcomputer are fixed to the different walls and the different uprights of the frame 8 in a known manner, with the aid of fastening and gripping collars, fastening braces, assembly plates, gripping plates and rods, fastening staples, as well as various types of screws and bolts. The supply of nitrogen will be assured, as shown in FIGS. 7 and 8, by a nitrogen container 48 through an expansion device 47 which permits lowering the pressure delivered by the nitrogen container from 200 bar to 15 bar for supplying through a control valve 51 two expansion valve 46-humidity filter 45 assemblies provided respectively for supplying the center 5 for adjustment and regulation. The nitrogen container 48 is disposed near the apparatus and connected to one of the distribution cylinders 3. The volumetric solvent proportioner 1-chemical reactor 2 assemblies are mounted in parallel by means of tubes 10 interconnected by unifying junctions 11, and in which are injected solvents or nitrogen, valves 12 being inserted in the tubes 10, by junctions 11' between valves 12 and tubes 10, the unifying junctions 11 and the valve-tube junctions 11' as well as the tubes 10 being realized in polytetrafluoroethylene (PTFE) or in fluorinated ethylenepropylene copolymer (FEP).

All the junctions are of a known type, perferably from the Bohlender society. The number of volumetric solvent proportioner 1-chemical reactor 2 assemblies may vary from one apparatus to other. In the embodiment described there will advantageously be six, that is to say six volumetric solvent proportioners 1 and six chemical reactors 2. It will therefore be possible to produce simultaneously six peptides of identical or different sequences and in different quantities. These latter may vary from about 100 milligrams to several grams. Each peptide will be realized in a volumetric solvent proportioner 1-chemical reactor 2 assembly, and this in a totally independent manner from the production of the other peptides.

Figure 2:
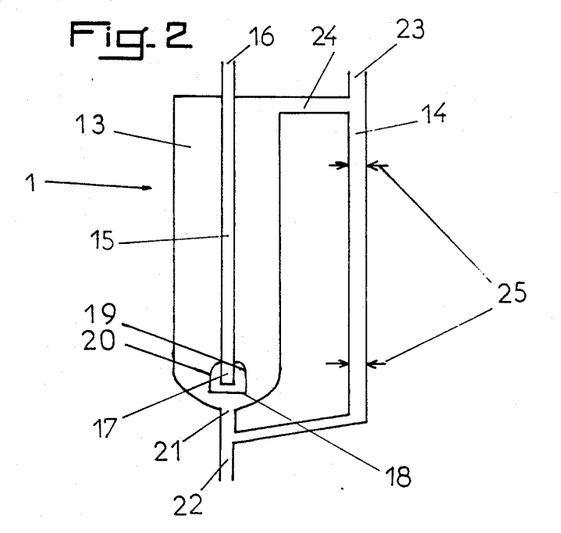
FIG. 2 is a sectional view of a volumetric proportioner.

As shown in FIG. 2, each volumetric solvent proportioner 1 is constituted by two cylinders, namely a principal cylinder 13 for introduction of the various solvents under pressure of nitrogen and a measuring column 14 for determination of the exact volume of solvent to be injected into the chemical reactor 2. The principal cylinder 13 is traversed by a column 15 the upper opening 16 of which is the principal inlet for the various solvents under pressure of nitrogen and projects with respect to the upper extremity of the principal cylinder 13, and the lower extremity 17 of which opens onto a disk 18 connected to the column 15 by two attachments 19 and 20, the lower extremity of the principal cylinder 13 being provided with an outlet opening 21 connected to a column 22 situated in the extension of the principal cylinder 13 for injection of a solvent under pressure of nitrogen into the chemical reactor 2. The measuring column 14 has, on the one hand, at its upper extremity an opening 23 for admittance of high pressure nitrogen and escape of air, connected, as shown in FIG. 8, to a device for evacuation under slight underpressure constituted by an activated charcoal filter 49 and an extractor 50, and, on the other hand, near this said upper extremity, a connection conduit 24 to the principal cylinder 13, its lower extremity being connected to the column 22. The measuring column 14 is associated with a strip 25 of optoelectronic detectors determining the various volumes of solvent. These optoelectronic detectors are advantageously positioned so as to select seven volumns of solvent, namely 5 ml, 20 ml, 30 ml, 40 ml, 50 ml, 60 ml and 70 ml. The preselection of the volume is realized by programming as a function of the quantity of product to be produced by the chemical reactor 2 which is associated with it. The volumetric solvent proportioners 1 thus permit simultaneously injecting various solvents in different quantities into the chemical reactors 2.

Figure 3:
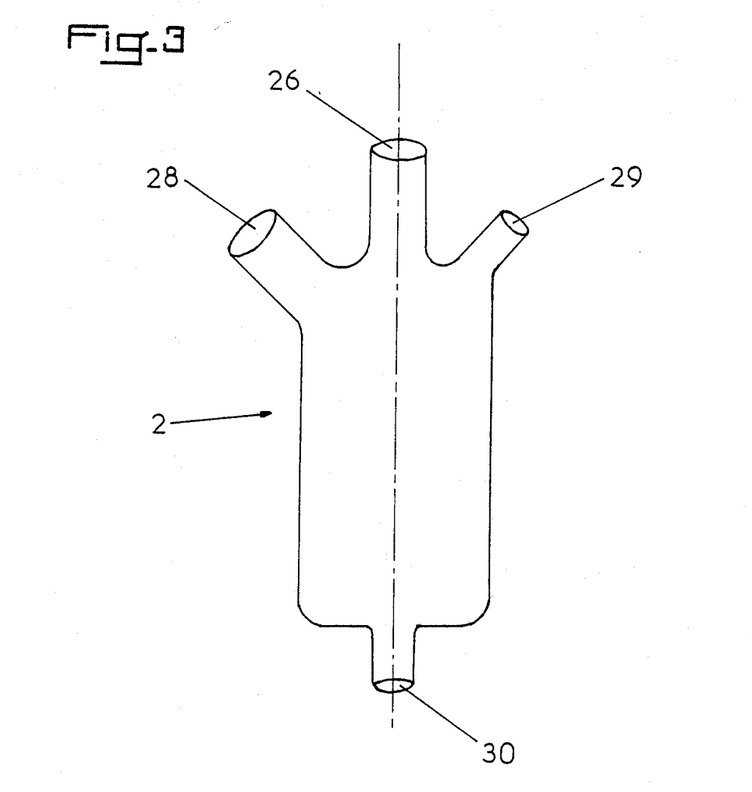
FIG. 3 is a sectional view of a chemical reactor.

According to FIG. 3, each chemical reactor 2 has four openings, namely an opening 26 situated at the top of the chemical reactor 2, containing an injection device 27 for solvent under pressure, as well as nitrogen under pressure at the time of evacuating the chemical reactor of its liquid, and connected by a T-shaped valves-junction assembly to the column 22 of the volumetric proportioner 1, an opening 28 for introduction of amino acids and of the resin similarly permitting the sample retention of the resin-peptide couples for the control, at the essential stages of the synthesis, and opening 29 connected, as shown in FIG. 8, to an evacuation device under weak underpressure constituted by an activated charcoal filter 49 and an extractor 50 for the evacuation of air or residual nitrogen retained in the chemical reactor 2 at the time of its refilling, the two openings 28 and 29 being situated on either side of the opening 26, and an opening 30 for evacuation of the solvents and admission of nitrogen under very low pressure for agitation by bubbling, and situated at the lower extremity of the chemical reactor 2. The experimenter places the resin in the interior of the various chemical reactors 2, resin to which is coupled the growing amino-acid chain. This latter thus undergoes a deprotection processing of the protecting t-butyloxycarbonyl groups by the various solvents, by means of successive washings. Then, after introduction under pressure of the solvent, the resin in suspension undergoes an agitation by bubbling with nitrogen under weak pressure.

According to another characteristic of the invention, all of the openings of the chemical reactor 2 are provided with control valves 12 assuring successively or simultaneously the control of the inlets and the outlets of the reactor and being able totally to isolate this latter from its peripheral context, the opening 30 situated at the lower extremity of the chemical reactor 2 being connected, as shown in FIGS. 7 and 8, on the one hand, to a waste valve 131 and, and on the other hand, to a bubbling valve 130 with the aid of a T-shaped connector 11".

Each chemical reactor 2, associated with each volumetric solvent proportioner 1, thus forms an assembly which is comprised as an independent entity. It is therefore possible to use one or several reactors 2, independently from one another, so as partially to isolate one or several during the course of the synthesis, to modulate the quantity of peptides produced by each one of the reactors 2, and, consequently, to be able to synthesize simultaneously variable quantities of peptides of different sequences.

Figure 4:
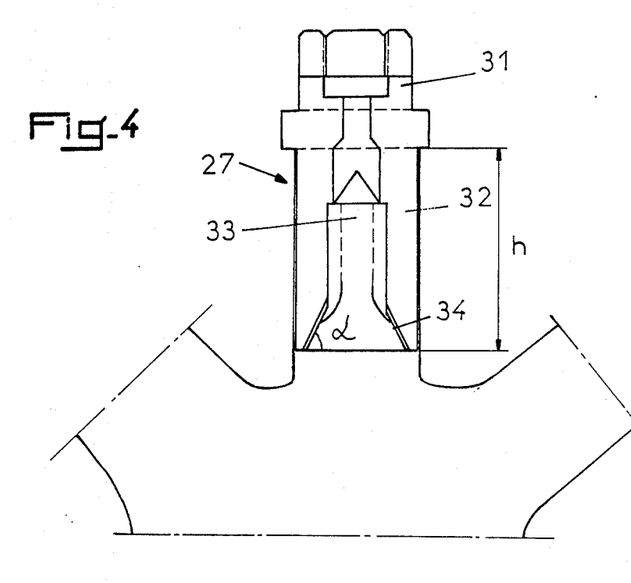
FIG. 4 is a sectional view of an injection device.

According to FIG. 4, the injection device 27 of the solvent under pressure has at its upper part a coupling connection 31, and is composed of a hollow cylinder 32, into which is introduced an open, ribbed cylinder 33, of slightly lesser diameter and having on its lower base an enlarged frustoconical portion 34 permitting a radial and laminar distribution of the liquid flux injected into the chemcial reactors 2.

The angle of the truncated cone 34 is preferably comprised between 50° and 70° and the height h of the injection device 27 inserted into the neck of the opening 26 is provided such that the liquid injected comes in contact of the internal wall of the chemical reactor 2 as well as the internal wall of the openings 28 and 29.

The height h of the injection device inserted into the neck of the opening 26 is preferably about 10 mm shorter than the length of the said neck. The diameter of the injection device 27 is less than the diameter of the neck of the opening 26 of the chemical reactor 2 by about 0.5 mm to 1.5 mm, such that the meniscus is formed between the wall of the glass and the lower extremity of the ribbed cylinder 33. Thus, the injected liquid recovers all the resin particles which may adhere to the internal wall of the chemical reactor 2 and simultaneously washes the openings 28 and 29 of the chemical reactor 2.

Figure 5:
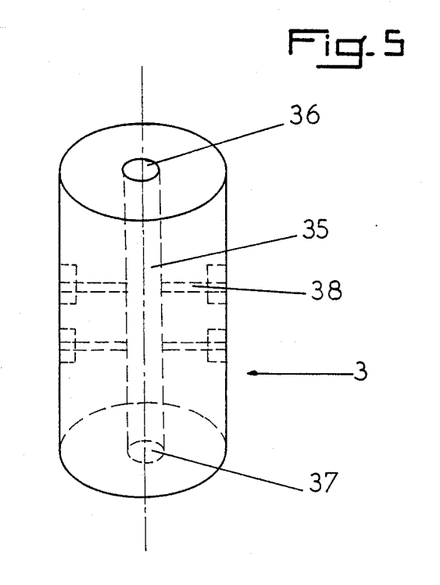
FIG. 5 is a perspective view of a distribution cylinder.

According to FIG. 5, each distribution cylinder 3 is provided with a concentric distribution channel 35, the extremities 36 and 37 of which form the inlet and the outlet of the distributor, the distribution being effected radially by means of channesl 38 disposed on different levels.

According to an embodiment, the channels 38 are advantageously eight in number and on two levels, namely four channels per level, and are disposed at 90° with respect to one another.

According to another characteristic of the invention, as shown in FIGS. 7 and 8, the number of distribution cylinders 3 is advantageously eight, namely a general distribution cylinder 3A for the solvents, a general distribution cylinder 3B for nitrogen, a distribution cylinder 3C for low pressure nitrogen toward the opening 16 of the volumetric proportioner 1 and for evacuation of air and nitrogen from the same opening 16, a distribution cylinder 3D for low pressure nitrogen toward the opening 29 of the chemical reactors 2 and for the evacuation of air and nitrogen from the same opening 29, a general distribution cylinder 3E for evacuation of air and nitrogen vapors toward a hood 44, a general distribution cylinder 3F for evacuation of the waste, a general distribution cylinder 3G for very low pressure nitrogen toward the opening 30 of the chemical reactors 2 and a distribution cylinder for nitrogen for the evacuation of the chemical reactor 2 (see FIGS. 7 and 8).

Figure 6:
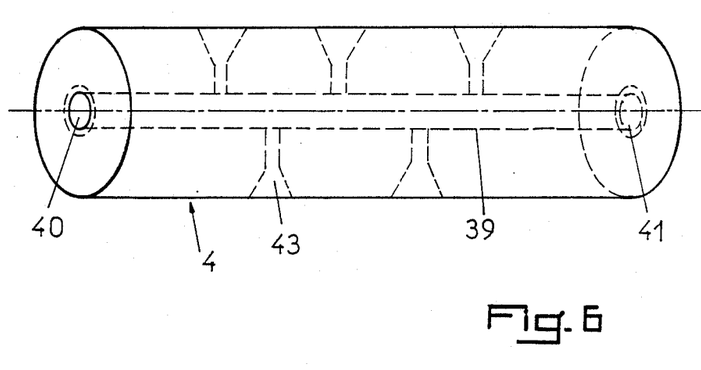
FIG. 6 is a perspective view of the solvent selector.

According to FIG. 6, the solvent selector 4 is traversed by a concentric distribution channel 39, one extremity 40 of which is connected by tubes 10 and connectors 11, 11' to one of the distribution cylinders 3 and the other extremity 41 of which is connected by tubes 10 and connectors 11, 11' to a waste recovery device 42, and the various solvents being supplied to the distribution channel 39 by means of channels 43 having openings controlled by valves 120 and each disposed on a different level according to the repeating interval of a helix. The solvent selector 4 is designed such that it eliminates any risk of contamination of the chemical reactors 2, momentarily isolated by segments of parasitic fluid. Specifically, at the time of the injection into the volumetric proportioners 1 of the most aggressive solvent, in this case trifluoroacetic acid, this latter contaminates on its passage the small injection channels 43 of the other solvents. But the channels 43 each being disposed on a different level according to the repeating interval of a helix so as to be able to sequence the following solvents in a very precise order, from the most aggressive to the least aggressive starting from the base of the solvent selector 4, they are well cleansed by a reflux motion of the liquid toward the waste recovery device 42. There is thus assured a complete rinsing of the solvent selector 4.

The distribution cylinders 3 as well as the solvent selector 4 are advantageously realized in PTFE.

The invention similarly has as an object a process for production of synthetic peptides by use of the peptide multisynthesizer shown in FIG. 1, the process consisting in realizing simultaneously and independently the synthesis of a variable number of peptides in different quantities, of identical or different sequences, according to a common synthesis technique comprising, for each cycle, either starting from an amino acid-resin couple that has been introduced into each chemical reactor 2, or such a couple to be realized for each volumetric solvent proportioner 1-chemical reactor 2 assembly, then deprotecting the N-α amino group of each amino acid by eliminating the t-butyloxycarbonyl protecting group by acidolysis and neutralizing the amino group obtained in the form of a salt, coupling the second protected amino acid to the resin, deprotecting its N-α amino group and repeating this cycle for each peptide to be produced, with identical or different sequence, a number of times equal to the number of amino acids to be fixed in the resin. This number of amino acids could therefore be different from one chemical reactor 2 to the other. The first peptide obtained will be that comprising the least amino acids and the last obtained will be that comprising the most, the duration of production of each peptide being proportional to the number of cycles required, and thus to the number of amino acids to be fixed in the resin.

The first step of each cycle of the synthesis technique consists, either in introducing a resin/amino acid couple through the opening 28 of each chemical reactor 2, or generating it with the aid of the multisynthesizer. For the generation of the resin/amino acid couples, the following steps, for each volumetric solvent proportioner 1-chemical reactor 2 assembly, are effected under the control of the programmable automaton 7 or the microcomputer:

manual introduction of resin through the opening 28;
injection of a solvent under pressure of nitrogen, namely dichloromethane, through the opening 26;
introduction of very low pressure nitrogen through the opening 30 for an agitation by bubbling of about 1 min. so as to wash and to inflate the resin by agitation of the solvent and the resin;
introduction of nitrogen under pressure through the opening 26 so as to evacuate the solvent through the opening 30;
repetition of these three latter operations until obtention of a suitable resin;
manual introduction of the amino acid protecting group t-butyloxycarbonyl through the opening 28;
injection of a solvent under pressure of nitrogen, namely dichloromethane, through the opening 26;
introduction of very low pressure nitrogen through the opening 30 for about 4 hours for an agitation by bubbling with manual introduction with several repetitions of coupling and/or activating agents through the opening 28;
introduction of nitrogen under pressure through the opening 26, so as to evacuate the solvent through the opening 30;
injection of a solvent under pressure of nitrogen; namely dichloromethane, through the opening 26;
introduction of very low pressure nitrogen through the opening 30 for about one minute for an agitation by bubbling so as to wash the resin-amino acid couple;
introduction of nitrogen under pressure through the opening 29, so as to evacuate the solvent through the opening 30;
repetition of these three letter operations until obtention of a suitable resin-amino acid couple.

There will thus follow, for each resin-amino acid couple obtained, the deprotection of the N-amino group, by elimination of the protecting group t-butyloxycarbonyl by acidolysis according to the following steps, affected under the control of the programmable automaton 7 or the microcomputer for each volumetric solvent proportioner 1-chemical reactor 2 assembly;
injection under pressure of nitrogen through the opening 26 of a mixture of 35% dichloromethane and 65% trifluoroacetic acid;
introduction of very low pressure nitrogen through the opening 30 for about one minute, for an agitation by bubbling;
introduction of nitrogen under pressure through the opening 26 so as to evacuate the dichloromethane-trifluoroacetic acid mixture through the opening 30;
injection of the mixture of dichloromethane and trifluoroacetic acid under pressure of nitrogen in equal proportions through the opening 26;
introduction for about 13 minutes of very low pressure nitrogen through the opening 30 for an agitation by bubbling;
introduction of nitrogen under pressure through the opening 26 so as to evacuate the dichloromethane-trifluoroacetic acid mixture through the opening 30;
injection of a solvent under pressure of nitrogen, namely dichloromethane, through the opening 26;
introduction of very low pressure nitrogen through the opening 30 for about one minute for an agitation by bubbling so as to wash the deprotected amino acid-resin couple;
introduction of nitrogen under pressure through the opening 26 so as to evacuate the solvent through the opening 30;
repetition of these three latter operations;
injection of a solvent under pressure of nitrogen, namely dimethylformamide through the opening 26, so as to eliminate the remaining trifluoroacetic acid;
introduction of very low pressure nitrogen through the opening 30 for several seconds, for an agitation by bubbling;
introduction of nitrogen under pressure through the opening 26 so as to evacuate the solvent through the opening 30;
injection of a solvent, namely dichloromethane, through the opening 26;
introduction of very low pressure nitrogen through the opening 30 for about one minute for an agitation by bubbling;
introduction of nitrogen under pressure through the opening 26 so as to evacuate the solvent through the opening 30;
injection of a solvent, namely dimethylformamide through the opening 26;
introduction of very low pressure nitrogen through the opening 30 for about one min. for an agitation by bubbling;
introduction of nitrogen under pressure through the opening 26 so as to evacuate the solvent through the opening 30;
repetition of this latter operation;

For the neutralization of the amino group obtained in the salt form, the following steps, for each volumetric solvent proportioner 1-chemical reactor 2 assembly are effected under the control of the programmable automaton 7 or the microcomputer:

injection under pressure of nitrogen of a mixture of 10% diisopropylethylamine and 90% dichloromethane or dimethylformamide through the opening 26;
introduction of very low pressure nitrogen through the opening 30 for about one min. for an agitation by bubbling;
introduction of nitrogen under pressure through the opening 26 so as to evacuate the diisopropylethylaminedichloromethane mixture or the diisopropylethylaminedimethylformamide mixture through the opening 30;
repetition of this latter operation;

injection of a solvent under pressure of nitrogen, namely dichloromethane or dimethylformamide, through the opening 26;

introduction of very low pressure nitrogen through the opening 30 for about one minute for an agitation by bubbling;

introduction of nitrogen under pressure through the opening 26 so as to evacuate the solvent through the opening 30;

repeating three times this latter operation for the washing of the resin-amino acid couple;

manual withdrawal through the opening 28 of a sample of the resin-amino acid couple for verification of the deprotection reaction with the aid of a test with ninhydrin.

Finally, for coupling the second protected amino acid onto the obtained resin-amino acic couple, the following steps, for each volumetric solvent proportioner 1-chemical reactor 2 assembly are realized under the control of the programmable automaton 7 or the microcomputer:

manual introduction of the protected amino acid, activated or non-activated, through the opening 28;

injection of a solvent under pressure of nitrogen, namely dichloromethane or dimethylformamide, through the opening 26;

introduction of very low pressure nitrogen through the opening 30 for a duration comprised between 10 and 60 minutes for an agitation by bubbling with manual introduction of coupling and/or activating agents through the opening 28;

manual withdrawal through the opening 28 of a sample of the obtained resin-amino acid assembly and test with ninhydrin;

either introduction of nitrogen under pressure through the opening 26 so as to evacuate the solvent through the opening 30, if the test effected at the time of the preceding operation is negative, or repeating of the operations starting from the neutralization of the amino group obtained in the salt form, if the test effected at the time of the said preceding operation is positive;

injection of a solvent under pressure of nitrogen, namely dichloromethane, through the opening 26;

introduction of very low pressure nitrogen through the opening 30 for about one minute for agitation by bubbling so as to wash the obtained resin-amino acid assembly;

introduction of nitrogen under pressure through the opening 26 so as to evacuate the solvent through the opening 30;

repeating three times this latter operation until obtention of a suitable assembly.

Throughout the cycle, the pressure of nitrogen necessary for injection of the solvent is comprised between 300 and 400 mbar, preferably between 340 and 360 mbar, and the pressure of nitrogen for the agitation by bubbling is comprised between 10 and 70 mbar, preferably between 20 and 35 mbar. This very low pressure is maintained constant within ±1/10 mbar thanks to the center 5 for adjustment and regulation of nitrogen. The volume of solvent to be injected is comprised between 15 and 25 ml/gram of resin, preferably 20 ml.

The programmable automaton 7 or microcomputer controls each physical element of the multisynthesizer, so as to cause it to execute the necessary functions throughout the course of each cycle of the synthesis technique. If it is a case of a programmable automaton, its microprocessor could advantageously be of the 8032 type from Intel Corp., the program memory of 4K octets ROM and the assembly program language MCS 51.

The programmable automaton or microcomputer thus controls the chronology of the various operations of each cycle, as well as each operation itself.

The principal operations for each cycle are the measuring of the solvent volumes, the injection of solvent into each chemical reactor 2, the agitation by bubbling and the evacuating of each chemical reactor 2.

According to a characteristic of the invention, the measuring of the solvent volumes to be injected into each chemical reactor 2 through the opening 26 is effected under the control of the programmable automaton or microcomputer 7 in the following manner:

opening of the valve 120 for admission of the selected solvent and 120' for admission of the selected nitrogen;

opening of the admission valve 121 of the opening 16 of the volumetric solvent proportioner 1;

opening of the valve 122 for exposing the distribution cylinder 3C to the ambient;

injection of a solvent under pressure of nitrogen through the opening 16 of the volumetric proportioner 1 until a detection of the level by the strip 25 of optoelectronic detectors;

closing of the admission valve 121 of the opening 16 of the volumetric solvent proportioner 1;

adjustment of the pre-established volume for each volumetric proportioner 1-chemical reactor 2 assembly;

closing the admission valves 120 and 120' for the solvent-nitrogen pair selected. According to another characteristic of the invention, the injection of solvent into each chemical reactor 2 is effected under the control of the programmable automaton 7 or microcomputer in the following manner:

opening of the valve 123 for admission of nitrogen from the distribution cylinder 3C so as to pressurize, through the opening 16 of the volumetric proportioner 1, the solvent contained in the principal cylinder 13 and the measuring column 14 of the volumetric proportioner 1;

placing in underpressure the chemcial reactor 2 by opening the expansion valve 125 of the opening 29 through the distribution cylinder 3D;

opening of the admission valve 126 of the opening 26;

placing in underpressure for about 5 seconds the volumetric proportioner 1 by opening the valve 122 for exposing the distribution cylinder 3C to the ambient.

According to another characteristic of the invention, the agitation by bubbling in each chemical reactor 2 is effected under the control of the programmable automaton 7 or microcomputer in the following manner:

placing the reactor in underpressure by opening the expansion valve 125 of the opening 29 through the distribution cylinder 3D;

delay of 5 seconds for relaxation of the chemical reactor 2;

opening general valves 127, 127' for distribution of very low pressure nitrogen above the distribution cylinder 3G;

opening the nitrogen admission valve 130 of the opening 30;

opening the valve 128 controlling the overpressure impulse for a half second;

closing the valve 128;

distribution of nitrogen at very low controlled pressure for an agitation by bubbling through the opening 30;

closing the nitrogen admission valve 130 of the opening 30;

delay of 200 ms prior to the beginning of evacuation.

According to another characteristic of the invention, the evacuation of each chemical reactor 2 is effected under the control of the programmable automaton or microcomputer 7 in the following manner:

opening the valve 126' of the opening 26 for admission of nitrogen from the distribution cylinder 3H;

opening the waste valve 124 of the distribution cylinder 3F;

opening the solvent evacuation valve 131 of the opening 30;

placing the reactor in underpressure by opening the waste valve 125 of the opening 29 through the distribution cylinder 3D;

delay of 5 seconds for relaxation of the chemical reactor 2.

The operations accompanying each cylinder are the rinsing of the solvent selector 4 and the refilling of the solvent container 6. The rinsing of the solvent selector 4 of the residual segments of preceding solvent is effected under the control of the programmable automaton 7 or microcomputer in the following manner:

opening the nitrogen admission valve 123 of the distribution cylinder 3C;

opening the waste valve 129 of the solvent selector 4;

opening of the admission valve 121 of the opening 16.

The refilling of the solvent containers, is effected under the control of the programmable automaton 7 or microcomputer in the following manner:

closing the low pressure valve 132 of the distribution cylinder 3B;

opening the valve 133 for exposing the distribution cylinder 3B to the ambient;

opening the valve 120' of the solvent container under consideration;

manual refilling of the containers 6;

closing the valve 120' of the solvent container under consideration;

closing the valve 133 for exposing the distribution cylinder 3B to the ambient;

opening the low pressure valve 132 of the distribution cylinder 3B.

Finally, the programmable automaton or the microcomputer similarly controls the liquid crystal display, the print-out, the injection of solvent for the compensation of evaporation during long periods of agitation by bubbling, as well as the alarm and safety devices.

It will be understood that the invention is not limited to the embodiments described and shown in the accompanying drawings. Modifications remain possible, particularly from the point of view of the construction of the various elements, or by substitution of equivalent techniques, without departing whatsoever from the scope of protection of the invention.

What is claimed is:

1. In a semi-automatic, solid phase peptide multi-synthesizer of the type comprising a hydraulic circuit having: a plurality of chemical reactors; a corresponding plurality of volumetric solvent proportioners, each of said plurality of chemical reactors being disposed downstream of a corresponding said volumetric solvent proportioner; a plurality of solvent containers disposed upstream of said plurality of volumetric solvent proportioners; distribution means disposed intermediate said solvent containers and said solvent proportioners, for directing a desired solvent from its corresponding said solvent container to any selected one of said plurality of volumetric solvent proportioners; and a programmable microcomputer implementing a predetermined sequence in which fluids are supplied to and evacuated from said plurality of chemical reactors and said corresponding plurality of volumetric solvent proportioners; the improvement in which said distribution means comprises a first cylindrical element traversed by an axial opening forming a distribution channel having inlet and outlet ends, a plurality of radial openings communicating with said distribution channel and offset axially of said cylindrical element, said cylindrical element being disposed substantially vertically within said multi-synthesizer such that said inlet end underlies said outlet end, each said radial opening being connected to a said volumetric solvent proportioner and said inlet end of said distribution channel receiving solvents from said solvent containers.

2. Peptide multi-synthesizer according to claim 1, further comprising a frame having a lower portion enclosing said plurality of solvent containers, a central portion comprising a work table above which are disposed said plurality of chemical reactors, and an upper portion enclosing said volumetric solvent proportioners, said distribution means and said programmable microcomputer.

3. Peptide multi-synthesizer according to claim 1, wherein said plurality of chemical reactors and said corresponding plurality of volumetric solvent proportioners are mounted in parallel by means of tubes interconnected by unifying connectors, said tubes comprising valves for isolating any selected one of said plurality of volumetric solvent proportioners and its corresponding said chemical reactor, said tubes and said unifying connectors being formed from polytetrafluoroethylene (PTFE) or fluorinated ethylenepropylene copolymer (FEP).

4. Peptide multi-synthesizer according to claim 1, wherein each of said plurality of volumetric solvent proportioners comprises a principal cylinder for introduction of solvents under pressure of nitrogen and a measuring column for determining exact volume of solvent to be injected into a corresponding said chemical reactor, said principal cylinder comprising a column having an upper opening forming a principal inlet for solvents under pressure of nitrogen, said column projecting upwardly and outwardly from said principal cylinder, said column having a lower end opening onto a disk connected to said column, said principal cylinder comprising a lower outlet communicable with its corresponding said chemical reactor, said measuring column having an upper inlet for reception of high pressure nitrogen and evacuation of air, evacuation means being connected to said upper inlet of said measuring column, said evacuation means comprising an activated charcoal filter and an extractor, said measuring column being in continuous communication with said principal column.

5. Peptide multi-synthesizer according to claim 1, wherein each of said plurality of chemical reactors comprises a first upper opening comprising an injection device for pressurized solvent, said first upper opening being communicable with its corresponding said volumetric solvent proportioner, a second upper opening for introduction of amino acids and resin and for withdrawing samples of peptide-resin couples, a third upper opening for evacuation of said reactor, evacuation means being connected to said third upper opening and comprising an activated charcoal filter and an extractor for evacuation of air or residual nitrogen contained in said reactor, said second and third upper openings flanking said first upper opening, and a lower opening for evacuation of solvents and admission of low pressure nitrogen for agitation by bubbling, all said openaings of said reactor comprising control valves permitting successive or simultaneous control of admission and evacuation of fluids from said reactor.

6. Peptide multi-synthesizer according to claim 5, wherein said injection device of said first upper opening of each said reactor comprises an upper coupling connector comprising a hollow cylinder containing an open, ribbed cylinder of slightly lesser diameter, said ribbed cylinder having a lower base comprising an enlarged frusto-conical portion permitting radial and laminar distribution of liquid flux injected into said reactor.

7. Peptide multi-synthesizer according to claim 6, wherein said enlarged frustoconical portion of said ribbed cylinder comprised by said injection device of said first upper opening of said chemical reactor defines a conical angle comprised between 50° and 70° and has a height about 10 mm less than said first upper opening of said reactor, whereby liquid injected through said injection device contacts interior surfaces of said chemical reactor and said second and third upper openings thereof.

8. Peptide multi-synthesizer according to claim 1, wherein said distribution means further comprises a second cylindrical element disposed vertically within said multi-synthesizer intermediate said solvent containers and said first cylindrical element, said second cylindrical element being traversed by an axial opening forming a distribution channel having first and second ends, a plurality of radial openings communicating with said distribution channel and each disposed on a different level of said second cylindrical element according to a helical repeating interval, each said radial opening of said second cylindrical element receiving solvent from a said solvent container, said upper end of said distribution channel of said first cylindrical element communicating with said inlet end of said distribution channel fo said first cylindrical element, said lower end of said distribution channel of said second cylindrical element communicating with a waste recovery device.

9. In a semi-automatic, solid phase peptide multi-synthesizer of the type comprising a hydraulic circuit having: a plurality of chemical reactors; a corresponding plurality of volumetric solvent proportioners, each of said plurality of chemical reactors being disposed downstream of a corresponding said volumetric solvent proportioner; a plurality of solvent containers disposed upstream of said plurality of volumetric solvent proportioners; distribution means disposed intermediate said solvent containers and said solvent proportioners, for directing a desired solvent from its corresponding said solvent container to any selected one of said plurality of volumetric solvent proportioners; and a programmable microcomputer implementing a predetermined sequence in which fluids are supplied to and evacuated from said plurality of chemical reactors and said corresponding plurality of volumetric solvent proportioners; the improvement in which each said volumetric solvent proportioner comprises a measuring column associated with a strip of optoelectronic level detectors, said computer being programmed to halt supply of solvent to each said volumetric solvent proportioner responsive to detection by its corresponding said detectors of solvent in said measuring column having attained a predetermined level.

* * * * *